United States Patent [19]

Agrawal

[11] Patent Number: 5,856,462
[45] Date of Patent: *Jan. 5, 1999

[54] OLIGONUCLEOTIDES HAVING MODIFIED CPG DINUCLEOSIDES

[75] Inventor: Sudhir Agrawal, Shrewsbury, Mass.

[73] Assignee: Hybridon Incorporated, Milford, Mass.

[*] Notice: This patent issued on a continued prosecution application filed under 37 CFR 1.53(d), and is subject to the twenty year patent term provisions of 35 U.S.C. 154(a)(2).

[21] Appl. No.: 711,568

[22] Filed: Sep. 10, 1996

[51] Int. Cl.$^6$ .................................................. C07H 21/04
[52] U.S. Cl. ...................... 536/24.5; 536/23.1; 536/24.3
[58] Field of Search ................................ 536/23.1, 24.5, 536/24.3; 514/44; 435/325, 6, 91.1, 375

[56] References Cited

U.S. PATENT DOCUMENTS

| | | | |
|---|---|---|---|
| 4,806,463 | 2/1989 | Goodchild et al. | 514/44 |
| 5,149,797 | 9/1992 | Pederson et al. | 536/24.5 |
| 5,194,428 | 3/1993 | Agrawal et al. | 514/44 |

FOREIGN PATENT DOCUMENTS

| | | |
|---|---|---|
| WO 93/13749 | 7/1993 | WIPO . |
| WO 94/02498 | 2/1994 | WIPO . |
| WO 94/26877 | 11/1994 | WIPO . |
| WO 95/09236 | 4/1995 | WIPO . |
| 9602555 | 2/1996 | WIPO . |
| WO 96/19572 | 6/1996 | WIPO . |

OTHER PUBLICATIONS

Paterson et al. (1977) *Proc. Natl. Acad. Sci. USA* 74:4370–4374.
Zamecnik et al. (1978) *Proc. Natl. Acad. Sci. USA* 75:280–284.
Tao et al. (1995) *Antisense Research & Development* 5:123–129.
Agrawal (1992) *Trends in Biotechnology* 10:152–158.
Agrawal et al (1995) *Current Opinion in Biotechnology* 6:12–19.
Agrawal et al. (1995) *Clinical Pharmacokinetics* 28:7–16.
Zhang et al. (1995) *Clinical Pharmacology and Therapeutics* 58:44–53.
Krieg et al. (1995) *Nature* 374:546–549.
Habus et al. (1996) *Bioorganic and Medicinal Chemistry Letters* 6:1393–1398.
Iyer et al. (1996) *Tetrahedron Letters* 37:1539–1542.
Iyer et al. (1995) *Tetrahedron Asymmetry* 6:1051–1054.
Dougherty et al. (1992) *J. Am. Chem. Soc.* 114:6254.
Iyer et al. (1995) *Nucleosides & Nucleotides* 14:1031–1035.
Beaucage, In *Protocols for Oligonucleotides and Analogs: Synthesis and Properties,* Agrawal (editor), Humana Press, Totowa, NJ, pp.33–61.
Agrawal et al. (1987) *Tetrahedron Letters* 28:3539–3542.
Padmapriya et al. (1994) *Antisense Research & Development* 4:185–189.
Stein et al. (1996) *Trends in Biotechnology* 14:147–149.
Ballas et al. (1996) *Journal of Immunology* 157:1840–1845.
Sproat (1995) *Journal of Biotechnology* 41:221–238.
Torrence et al. (1993) *PNAS* 90:1300–1304.
Agrawal (1996) *Trends in Biotechnology* 14:376–387.
Krieg et al. Antisense & Nucleic Acid Drug Devel. 6:133–139 (1996).
Zhao et al. Biochem. Pharm. 51: 173–182 (1996).

*Primary Examiner*—John L. LeGuyader
*Attorney, Agent, or Firm*—Hale and Dorr LLP

[57] ABSTRACT

The invention relates to modified oligonucleotides that are useful for studies of gene expression and for the antisense therapeutic approach. The invention provides modified oligonucleotides that inhibit gene expression and that produce fewer side effects than conventional phosphorothioate oligonucleotides. In particular, the invention provides modified CpG-containing oligonucleotides that result in reduced splenomegaly and platelet depletion when administered to a mammal, relative to conventional CpG-containing phosphorothioate oligonucleotides. The invention further provides methods for using such oligonucleotides to modulate gene expression in vivo, including such use for therapeutic treatment of diseases caused by aberrant gene expression.

7 Claims, 2 Drawing Sheets

OLIGONUCLEOTIDES HAVING MODIFIED CPG DINUCLEOSIDES

BACKGROUND OF THE INVENTION

1. Field of the Invention

The invention relates to modified oligonucleotides that are useful for studies of gene expression and for the antisense therapeutic approach.

2. Summary of the Related Art

The potential for using oligonucleotides as inhibitors of specific gene expression in an antisense therapeutic approach was first suggested in three articles published in 1977 and 1978. Paterson et al., Proc. Natl. Acad. Sci. USA 74: 4370–4374 (1977) discloses that cell-free translation of mRNA can be inhibited by binding a complementary oligonucleotide to the mRNA. Zamecnik and Stephenson, Proc. Natl. Acad. Sci. USA 75: 280–284 and 285–288 (1978) disclose that a 13-mer synthetic oligonucleotide that is complementary to a part of the Rous sarcoma virus (RSV) genome can inhibit RSV replication in infected cell cultures and can inhibit RSV-mediated transformation of primary chick fibroblasts into malignant sarcoma cells.

Since these early studies, the ability of antisense oligonucleotides to inhibit virus propagation has become firmly established. U.S. Pat. No. 4,806,463 teaches that human immunodeficiency virus propagation can be inhibited by oligonucleotides that are complementary to any of various regions of the HIV genome. U.S. Pat. No. 5,194,428 discloses inhibition of influenza virus replication by phosphorothioate oligonucleotides complementary to the influenza virus polymerase 1 gene. Agrawal, Trends in Biotechnology 10: 152–158 (1992) reviews the use of antisense oligonucleotides as antiviral agents.

Antisense oligonucleotides have also been developed as anti-parasitic agents. PCT publication no. WO93/13740 discloses the use of antisense oligonucleotides to inhibit propagation of drug-resistant malarial parasites. Tao et al., Antisense Research and Development 5: 123–129 (1995) teaches inhibition of propagation of a schistosome parasite by antisense oligonucleotides.

More recently, antisense oligonucleotides have shown promise as candidates for therapeutic applications for diseases resulting from expression of cellular genes. PCT publication no. WO95/09236 discloses reversal of beta amyloid-induced neuronal cell line morphological abnormalities by oligonucleotides that inhibit beta amyloid expression. PCT publication no. WO94/26887 discloses reversal of aberrant splicing of a globin gene transcript by oligonucleotides complementary to certain portions of that transcript. PCT application no. PCT/US94/13685 discloses inhibition of tumorigenicity by oligonucleotides complementary to the gene encoding DNA methyltransferase.

The development of various antisense oligonucleotides as therapeutic and diagnostic agents has recently been reviewed by Agrawal and Iyer, Current Opinion in Biotechnology 6: 12–19 (1995).

As interest in the antisense therapeutic approach has grown, various efforts have been made to improve the pharmacologic properties of oligonucleotides by modifying the sugar-phosphate backbone. U.S. Pat. No. 5,149,797 describes chimeric oligonucleotides having a phosphorothioate core region interposed between methylphosphonate or phosphoramidate flanking regions. PCT publication no. WO94/02498 discloses hybrid oligonucleotides having regions of 2'-O-substituted ribonucleotides flanking a DNA core region.

Much is currently being discovered about the pharmacodynamic properties of oligonucleotides. Agrawal et al., Clinical Pharmacokinetics 28: 7–16 (1995) and Zhang et al., Clinical Pharmacology and Therapeutics 58: 44–53 (1995) disclose pharmacokinetics of anti-HIV oligonucleotides in human patients. Some of these new discoveries have led to new challenges to be overcome for the optimization of oligonucleotides as therapeutic agents. For example, Kniep et al., Nature 374: 546–549 (1995) discloses that oligonucleotides containing the CG dinucleotide flanked by certain other sequences have a mitogenic effect. We have discovered that many side effects produced by phosphorothioate oligonucleotides are a consequence of the phosphorothioate-linked CpG dinucleotide. There is, therefore, a need for modified oligonucleotides that retain gene expression inhibition properties while producing fewer side effects than conventional phosphorothioate oligonucleotides.

BRIEF SUMMARY OF THE INVENTION

The invention relates to modified oligonucleotides that are useful for studies of gene expression and for the antisense therapeutic approach. The invention provides modified oligonucleotides that inhibit gene expression and that produce fewer side effects than conventional phosphorothioate oligonucleotides. In particular, the invention provides methods for using CpG-containing phosphorothioate oligonucleotides to modulate gene expression with reduced splenomegaly and reduced depletion of platelets, relative to conventional CpG-containing phosphorothioate oligonucleotides.

In a first aspect, the invention provides modified CpG-containing phosphorothioate oligonucleotides and compositions of matter for inhibiting specific gene expression with reduced side effects. Such inhibition of gene expression can be used as an alternative to mutant analysis for determining the biological function of specific genes in cell or animal models. Such inhibition of gene expression can also be used to therapeutically treat diseases that are caused by expression of the genes of a virus or a pathogen, or by the inappropriate expression of cellular genes. In one preferred embodiment according to this aspect of the invention, the composition of matter comprises phosphorothioate oligonucleotides having one or more modified CpG dinucleoside. In certain particularly preferred embodiments, all CpG dinucleosides present in the oligonucleotide are modified. According to this aspect of the invention, a CpG dinucleoside is modified so that it confers upon the oligonucleotide a reduced ability to cause splenomegaly and platelet depletion when administered to a mammal, relative to an otherwise identical oligonucleotide having an unmodified phosphorothioate CpG dinucleoside.

In a second aspect, the invention provides a method for modulating gene expression in a mammal with reduced side effects. In the method according to this aspect of the invention, a composition of matter according to the first aspect of the invention is administered to the mammal, wherein the oligonucleotide is complementary to a gene that is being expressed in the mammal.

In a third aspect, the invention provides a method for therapeutically treating, with reduced side effects, a disease caused by aberrant gene expression, the method comprising administering to an individual having the disease a composition of matter according to the first aspect of the invention, wherein the oligonucleotide is complementary to a gene that is aberrantly expressed, wherein such aberrant expression causes the disease. In this context, aberrant gene expression means expression in a host organism of a gene required for the propagation of a virus or a prokaryotic or eukaryotic pathogen, or inappropriate expression of a host cellular gene. Inappropriate host cellular gene expression includes expression of a mutant allele of a cellular gene, or underexpression or overexpression of a normal allele of a cellular gene, such that disease results from such inappropriate host cellular gene expression.

DETAILED DESCRIPTION OF THE PREFERRED EMBODIMENTS

Figure 1:
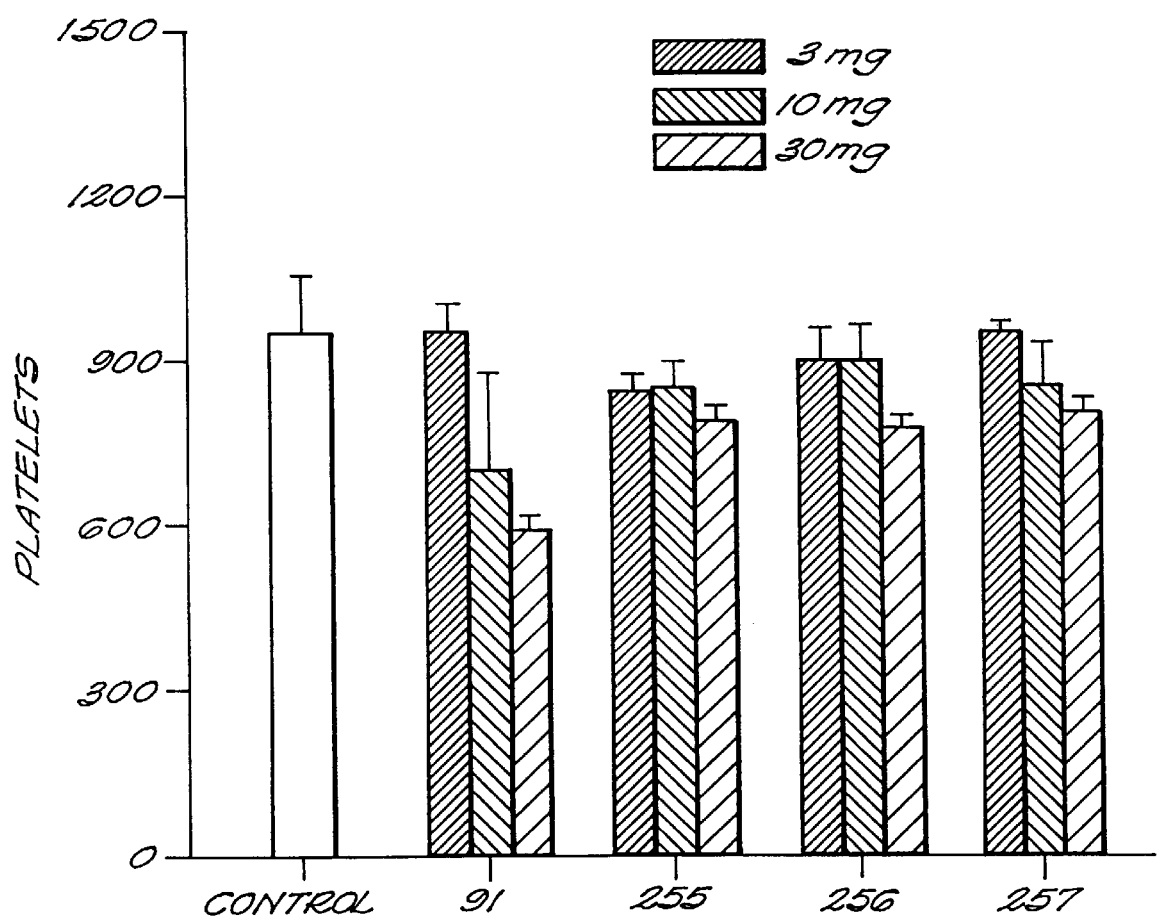
FIG. 1 shows results of platelet counts of CD1 mice intraperitoneally administered saline, conventional phosphorothioate oligonucleotide (91), methylphosphonate-modified CpG oligonucleotide(255), inverted CpG oligonucleotide (256), and 5-methylC CpG oligonucleotide (257).
Figure 2:
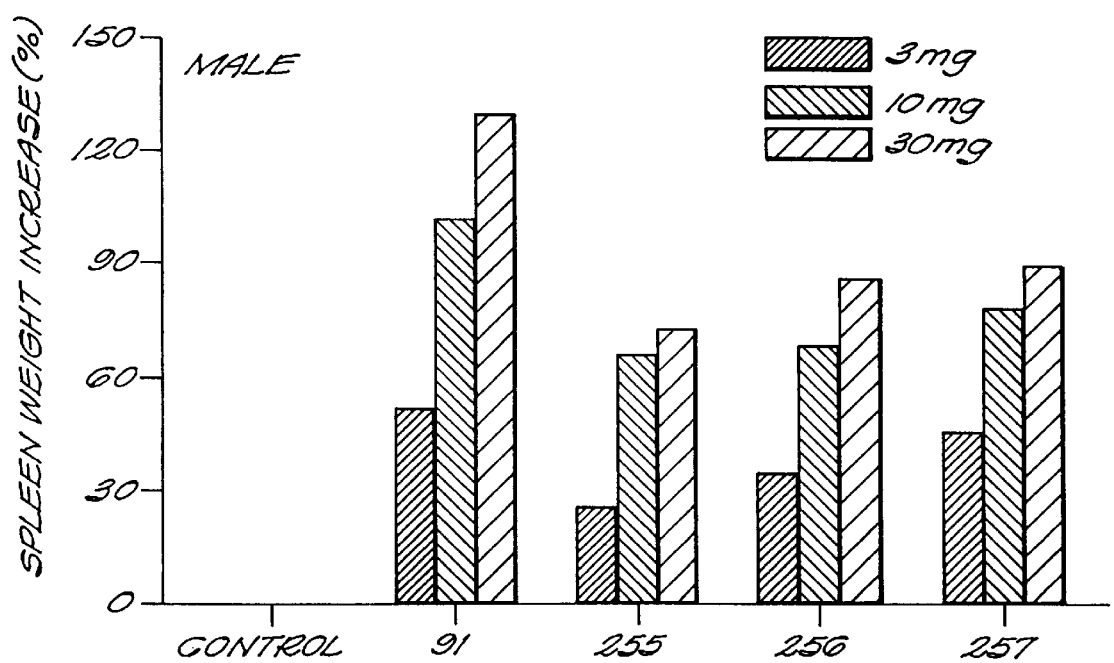
FIG. 2 shows results of spleen weight analysis of CD1 mice intraperitoneally administered saline, conventional phosphorothioate oligonucleotide (91), methylphosphonate-modified CpG oligonucleotide(255), inverted CpG oligonucleotide (256), and 5-methylC CpG oligonucleotide (257).

The invention relates to modified oligonucleotides that are useful for studies of gene expression and for the antisense therapeutic approach. All US patents, patent publications and scientific literature cited in this specification evidence the level of knowledge in this field and are hereby incorporated by reference.

The invention provides modified oligonucleotides that inhibit gene expression and that produce fewer side effects than conventional phosphorothioate oligonucleotides. In particular, the invention provides modified CpG-containing oligonucleotides that result in reduced splenomegaly and platelet depletion when administered to a mammal, relative to conventional CpG-containing phosphorothioate oligonucleotides. The invention further provides methods for using such oligonucleotides to modulate gene expression in vivo, including such use for therapeutic treatment of diseases caused by aberrant gene expression.

In a first aspect, the invention provides modified CpG-containing phosphorothioate oligonucleotides and compositions of matter for inhibiting specific gene expression with reduced side effects. Such inhibition of gene expression can be used as an alternative to mutant analysis for determining the biological function of specific genes in cell or animal models. Such inhibition of gene expression can also be used to therapeutically treat diseases that are caused by expression of the genes of a virus or a pathogen, or by the inappropriate expression of cellular genes.

In one preferred embodiment according to this aspect of the invention, the composition of matter comprises phosphorothioate oligonucleotides having one or more modified CpG dinucleoside. The CpG dinucleoside is 5'-CpG-3', i.e., in the 5' to 3' direction, a C nucleoside covalently linked to a G nucleoside through an internucleoside linkage. For purposes of the invention, CpG dinucleoside is considered to be "unmodified" if the internucleoside linkage is a racemic phosphorothioate linkage and the 5-position of the C nucleoside is occupied by a hydrogen atom. In certain particularly preferred embodiments, all CpG dinucleosides present in the oligonucleotide are modified. For purposes of the invention, a CpG dinucleoside is "modified" if it is altered from the unmodified CpG dinucleoside such that it confers upon the oligonucleotide a reduced ability to cause splenomegaly and platelet depletion when administered to a mammal, relative to an otherwise identical oligonucleotide having an unmodified phosphorothioate CpG dinucleoside. A composition of matter for inhibiting specific gene expression with reduced side effects, according to this aspect of the invention, comprises a modified CpG-containing phosphorothioate oligonucleotide that is complementary to a portion of a genomic region or gene for which inhibition of expression is desired, or to RNA transcribed from such a gene. For purposes of the invention, the term oligonucleotide includes polymers of two or more deoxyribonucleotide, ribonucleotide, or 2'-O-substituted ribonucleotide monomers, or any combination thereof. The term oligonucleotide also encompasses such polymers having chemically modified bases or sugars and/or having additional substituents, including without limitation lipophilic groups, intercalating agents, diamines and adamantane. For purposes of the invention, the term "phosphorothioate oligonucleotide" means an oligonucleotide containing at least one phosphorothioate internucleoside linkage, preferably from about 20% to about 100% phosphorothioate internucleoside linkages, and most preferably from about 50% to about 100% phosphorothioate internucleoside linkages. Preferably, such oligonucleotides will have from about 12 to about 50 nucleotides, most preferably from about 17 to about 35 nucleotides. For purposes of the invention the term "2'-O-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group, but not with a 2'-H group. The term "complementary" means having the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such hybridization can be inferred from the observation of specific gene expression inhibition. The gene sequence or RNA transcript sequence to which the modified oligonucleotide sequence is complementary will depend upon the biological effect that is sought to be modified. In some cases, the genomic region, gene, or RNA transcript thereof may be from a virus. Preferred viruses include, without limitation, human immunodeficiency virus (type 1 or 2), influenza virus, herpes simplex virus (type 1 or 2), Epstein-Barr virus, cytomegalovirus, respiratory syncytial virus, influenza virus, hepatitis B virus, hepatitis C virus and papilloma virus. In other cases, the genomic region, gene, or RNA transcript thereof may be from endogenous mammalian (including human) chromosomal DNA. Preferred examples of such genomic regions, genes or RNA transcripts thereof include, without limitation, sequences encoding vascular endothelial growth factor (VEGF), beta amyloid, DNA methyltransferase, protein kinase A, ApoE4 protein, p-glycoprotein, c-MYC protein, BCL-2 protein and CAPL. In yet other cases, the genomic region, gene, or RNA transcript thereof may be from a eukaryotic or prokaryotic pathogen including, without limitation, *Plasmodium falciparum, Plasmodium malarie, Plasmodium ovale, Schistosoma spp.,* and *Mycobacterium tuberculosis*.

In addition to the modified oligonucleotide according to the invention, the composition of matter for inhibiting gene expression with reduced side effects may optionally contain any of the well known pharmaceutically acceptable carriers or diluents. This composition of matter may further contain one or more additional oligonucleotides according to the invention. Alternatively, this composition may contain one or more traditional antisense oligonucleotide, such as an oligonucleotide phosphorthioate, a hybrid oligonucleotide, or a chimeric oligonucleotide, or it may contain any other pharmacologically active agent.

In one preferred embodiment according to this aspect of the invention, the modified CpG dinucleotide is selected from alkylphosphonate CpG, inverted CpG, 5-methylcytosine CpG, stereospecific phosphorothioate CpG, phosphotriester CpG, phosphoramidate CpG and 2'–5' CpG.

An alkylphosphonate CpG is a CpG dinucleoside in which the C nucleoside and the G nucleoside are covalently linked to each other through an alkylphosphonate internucleoside linkage. Alkylphosphonate CpG-containing oligonucleotides are conveniently prepared by using any conventional solid phase synthesis protocol to produce the CpG-containing oligonucleotide, except that the alkylphosphonate CpG dinucleoside is prepared using any standard procedure for introducing alkylphosphonate internucleoside linkages into oligonucleotides. One particularly preferred procedure for this step is described in Iyer et al., Bioorganic and Medicinal Chemistry Letters 6: 1393–1398 (1996). Preferably, the alkyl moiety of the alkylphosphonate linkage is a lower alkyl moiety of 1–6 carbon atoms, which may optionally be unsaturated and/or substituted. Most preferably, the alkylphosphonate CpG is a methylphosphonate CpG.

An inverted CpG is a 5'-GpC-3' dinucleoside. Inverted CpG-containing oligonucleotides are conveniently prepared by using any conventional solid phase synthesis protocol to produce the oligonucleotide, except that a G monomer synthon is used in place of the C monomer synthon and visa-versa.

A 5-methylC CpG is a CpG dinucleoside in which the C nucleoside is methylated at the 5 position of the cytosine base. 5-methylC CpG-containing oligonucleotides are conveniently prepared by using any conventional solid phase synthesis protocol to produce the oligonucleotide, except that a 5-methylC monomer synthon is used in place of the C monomer synthon.

A phosphotriester CpG is a CpG dinucleoside in which the C nucleoside and the G nucleoside are covalently linked to each other through a phosphotriester internucleoside linkage. Phosphotriester CpG-containing oligonucleotides are conveniently prepared by using any conventional solid phase synthesis protocol to produce the CpG-containing oligonucleotide, except that the phosphotriester CpG dinucleoside is prepared using any standard procedure for introducing phosphotriester internucleoside linkages into oligonucleotides. One particularly preferred procedure for this step is described in Iyer et al., Tetrahedron Letters 37: 1539–1542 (1996). Preferably, the phosphotriester linkage is a methylphosphotriester linkage.

A phosphoramidate CpG is a CpG dinucleoside in which the C nucleoside and the G nucleoside are covalently linked to each other through a phosphoramidate internucleoside linkage. Phosphoramidate CpG-containing oligonucleotides are conveniently prepared by using any conventional solid phase synthesis protocol to produce the CpG-containing oligonucleotide, except that the phosphoramidate CpG dinucleoside is prepared using any standard procedure for introducing phosphoramidate internucleoside linkages into oligonucleotides. One particularly preferred procedure for this step is described in Iyer et al., Tetrahedron Letters 37: 1539–1542 (1996). Most preferably, the phosphoramidate internucleoside linkage is a primary phosphoramidate internucleoside linkage.

A stereospecific phosphorothioate CpG is a CpG dinucleoside in which the C nucleoside and the G nucleoside are covalently linked to each other through a stereospecific phosphorothioate internucleoside linkage. Stereospecific phosphorothioate CpG-containing oligonucleotides are conveniently prepared by using any conventional solid phase synthesis protocol to produce the CpG-containing oligonucleotide, except that the phosphoramidate CpG dinucleoside is prepared using a procedure for introducing stereospecific phosphorothioate internucleoside linkages into oligonucleotides, preferably as described in Iyer et al., Tetrahedron Asymmetry 6: 1051–1054 (1995).

A 2'–5' CpG is a CpG dinucleoside in which the C nucleoside and the G nucleoside are covalently linked to each other through a 2'–5' internucleoside linkage. The internucleoside linkage may be of any type, and is preferably a phosphorothioate or phosphodiester linkage. 2'–5' CpG-containing oligonucleotides are conveniently prepared by using any conventional solid phase synthesis protocol to produce the CpG-containing oligonucleotide, except that the 2'–5' CpG dinucleoside is prepared using a procedure for introducing stereospecific phosphorothioate internucleoside linkages into oligonucleotides, for example as described in Dougherty et al., J. Am. Chem. Soc. 114: 6254 (1992) or Hashimoto and Switzer, Other modifications of the CpG dinucleoside include substitution of the phosphorothioate internucleoside linkage with any other internucleoside linkage, including without limitation phosphorodithioate, alkylphosphonothioate, siloxane, carbonate, carboxymethylester, acetamidate, carbamate, thioether, amide (PNA), bridged phosphoramidate, bridged methylene phosphonate, bridged phosphorothioate and sulfone internucleotide linkages.

In certain preferred embodiments of compositions according to this aspect of the invention, the oligonucleotides will be configured as "chimeric" or "hybrid" oligonucleotides, for example as described respectively in U.S. Pat. No. 5,149,797 and PCT publication no. WO94/02498. Briefly, chimeric oligonucleotides contain oligonucleotide regions having ionic internucleoside linkages as well as oligonucleotide regions having nonionic internucleoside linkages. Hybrid oligonucleotides have oligonucleotide regions containing DNA as well as oligonucleotide regions containing RNA or 2'-O-substituted RNA. Those skilled in the art will recognize that the elements of these preferred embodiments can be combined and the inventor does contemplate such combination. For example, 2'-O-substituted ribonucleotide regions may well include from one to all nonionic internucleoside linkages. Alternatively, nonionic regions may have from one to all 2'-O-substituted ribonucleotides. Moreover, oligonucleotides according to the invention may contain 2'-O-substituted or nonionic regions in the core region of the oligonucleotide flanked by phosphorothioate-containing DNA regions, or visa-versa, and further may contain combinations of one or more 2'-O-substituted ribonucleotide region and one or more nonionic region, either or both being flanked by phosphorothioate regions. (See Nucleosides & Nucleotides 14: 1031–1035 (1995) for relevant synthetic techniques).

In a second aspect, the invention provides a method for modulating gene expression in a mammal with reduced side effects. In the method according to this aspect of the invention, a composition of matter according to the first aspect of the invention is administered to the mammal, wherein the oligonucleotide is complementary to a gene that is being expressed in the mammal. Preferably, such adminisration may be parenteral, oral, intranasal or intrarectal. Preferably, a total dosage of oligonucleotide will range from about 0.1 mg oligonucleotide per kg body weight per day to about 200 mg oligonucleotide per kg body weight per day. In a preferred embodiment, after the composition of matter is administered, the biological effects of splenomegaly and platelet depletion are reduced, relative to the same effects obtained upon administration of an otherwise identical composition containing the same quantity of an otherwise identical oligonucleotide, except that such oligonucleotide contains an unmodified CpG dinucleoside in place of the modified CpG dinucleoside. This preferred biological effect can be monitored by measuring blood levels of platelets before and after oligonucleotide administration. Preferably, platelets will be depleted by less than about 20%, most preferably by less than about 10%.

In a third aspect, the invention provides a method for therapeutically treating, with reduced side effects, a disease caused by aberrant gene expression, the method comprising administering to an individual having the disease a composition of matter according to the first aspect of the invention, wherein the oligonucleotide is complementary to a gene that is aberrantly expressed, wherein such aberrant expression causes the disease. Thus, this is a preferred example of a method for modulating gene expression in a mammal, as discussed above for the second aspect of the invention. In this context, aberrant gene expression means expression in a host organism of a gene required for the propagation of a virus or a prokaryotic or eukaryotic pathogen, or inappropriate expression of a host cellular gene. Inappropriate host cellular gene expression includes expression of a mutant allele of a cellular gene, or underexpression or overexpression of a normal allele of a cellular gene, such that disease results from such inappropriate host cellular gene expression. Preferably, such administration should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may desirable to administer simultaneously, or sequentially a therapeutically effective amount of one or more of the therapeutic compositions of the invention to an individual as a single treatment episode. In a preferred embodiment, after the composition of matter is administered, the biological effects of splenomegaly and platelet depletion are reduced, relative to the same effects obtained upon administration of an otherwise identical composition containing the same quantity of an otherwise identical oligonucleotide, except that such oligonucleotide contains an unmodified CpG dinucleoside in place of the modified CpG dinucleoside. This preferred biological effect can be monitored by measuring blood levels of platelets before and after oligonucleotide administration. Preferably, platelets will be depleted by less than about 20%, most preferably by less than about 10%.

The following examples are intended to further illustrate certain preferred embodiments of the invention and are not intended to limit the scope of the invention.

EXAMPLE 1

Synthesis, Deprotection and Purification of Oligonucleotides

Oligonucleotide phosphorothioates were synthesized using an automated DNA synthesizer (Model 8700, Biosearch, Bedford, Mass.) using a beta-cyanoethyl phosphoramidite approach on a 10 micromole scale. To generate the phosphorothioate linkages, the intermediate phosphite linkage obtained after each coupling was oxidized using 3 H, 1,2-benzodithiole-3 H-one-1,1-dioxide (See Beaucage, In *Protocols for Oligonucleotides and Analogs: Synthesis and Properties*, Agrawal (editor), Humana Press, Totowa, N.J., pp. 33–62 (1993).) Similar synthesis was carried out to generate phosphodiester linkages, except that a standard oxidation was carried out using standard iodine reagent. Synthesis of methylphosphonate CpG-containing oligonucleotide was carried out in the same manner, except that methylphosphonate linkages were assembled using nucleoside methylphosphonamidite (Glen Research, Sterling, Va.), followed by oxidation with 0.1M iodine in tetrahydrofuran/2,6-lutidine/water (75:25:0.25) (see Agrawal & Goodchild, Tet. Lett. 28: 3539–3542 (1987). Deprotection and purification of oligonucleotides was carried out according to standard procedures, (See Padmapriya et al., Antisense Res. & Dev. 4: 185–199 (1994)), except for oligonucleotides containing methylphosphonate-containing regions. For those oligonucleotides, the CPG-bound oligonucleotide was treated with concentrated ammonium hydroxide for 1 hour at room temperature, and the supernatant was removed and evaporated to obtain a pale yellow residue, which was then treated with a mixture of ethylenediamine/ethanol (1:1 v/v) for 6 hours at room temperature and dried again under reduced pressure.

EXAMPLE 2

Reduced In Vivo Splenomegaly Using Modified CpG-Containing Oligonucleotides

Fischer rats were injected intravenously daily for seven days with a dose ranging from 3–30 mg/kg body weight of CpG-containing phosphorothioate oligonucleotide, methylphosphonate CpG-containing phosphorothioate oligonucleotide, inverted CpG-containing phosphorothioate oligonucleotide, 5-methylC CpG-containing phosphorothioate oligonucleotide, or saline as a control. On day 8, the animals were euthanized and the spleens were removed and weighed. Animals treated with methylphosphonate CpG-containing phosphorothioate oligonucleotide, inverted CpG-containing phosphorothioate oligonucleotide, or 5-methylC CpG-containing phosphorothioate oligonucleotide showed significantly less increase in spleen weight than those treated with CpG-containing oligonucleotide phosphorothioates. Similar results are expected to be observed for phosphotriester CpG-containing phosphorothioate oligonucleotides, phosphoramidate CpG-containing phosphorothioate oligonucleotides and 2'–5' CpG-containing phosphorothioate oligonucleotides.

EXAMPLE 3

Reduced In Vivo Platelet Depletion Using Modified CPG-Containing Oligonucleotides Fischer rats were injected intravenously daily for seven days with a dose ranging from 3–30 mg/kg body weight of CpG-containing phosphorothioate oligonucleotide, methylphosphonate CpG-containing phosphorothioate oligonucleotide, inverted CpG-containing phosphorothioate oligonucleotide, 5-methylC CpG-containing phosphorothioate oligonucleotide, or saline as a control. At day 8, blood was taken from the animals and platelet counts were taken. Animals treated with methylphosphonate CpG-containing phosphorothioate oligonucleotide, inverted CpG-containing phosphorothioate oligonucleotide, or 5-methylC CpG-containing phosphorothioate oligonucleotide showed significantly less depletion of platelets than those treated with CpG-containing oligonucleotide phosphorothioates. Similar results are expected to be observed for phosphotriester CpG-containing phosphorothioate oligonucleotides, phosphoramidate CpG-containing phosphorothioate oligonucleotides and 2'–5' CpG-containing phosphorothioate oligonucleotides.

What is claimed is:

1. A oligonucleotide for inhibiting specific gene expression with reduced side effects, the composition comprising a modified CpG-containing phosphorothioate oligonucleotide that is complementary to a portion of a genomic region or gene for which inhibition of expression is desired, or to RNA transcribed from such a gene, wherein the modified CpG is selected from alkylphosphonate CpG, inverted CpG, stereospecific phosphorotioate CpG, phosphotriester CpG, phosphoramidate CpG and 2'–5' CpG.

2. The oligonucleotide according to claim 1, wherein the modified CpG is a alkylphosphonate CpG.

3. The oligonucleotide according to claim 1, wherein the modified CpG is an inverted CpG.

4. The oligonucleotide according to claim 1, wherein the modified CpG is a stereospecific phosphorothioate CpG.

5. The oligonucleotide according to claim 1, wherein the modified CpG is a phosphotriester CpG.

6. The oligonucleotide according to claim 1, wherein the modified CpG is a phosphoramidate CpG.

7. The oligonucleotide according to claim 1, wherein the modified CpG is a 2'–5' CpG.

* * * * *